United States Patent [19]

Ryan

[11] Patent Number: 4,753,875
[45] Date of Patent: Jun. 28, 1988

[54] METHOD FOR ASSAYING PROTEASES WITH TAGGED PROTEINACEOUS INHIBITORS

[76] Inventor: James W. Ryan, 3420 Poinciana Ave., Miami, Fla. 33133

[21] Appl. No.: 759,355

[22] Filed: Jul. 26, 1985

Related U.S. Application Data

[63] Continuation of Ser. No. 317,411, Nov. 2, 1981, abandoned.

[51] Int. Cl.$^4$ .................... G01N 33/573; C12Q 1/56; C12Q 1/38; C12N 9/99
[52] U.S. Cl. .......................................... 435/7; 435/13; 435/23; 435/184
[58] Field of Search .................... 435/7, 8, 13, 23, 184

[56] References Cited

U.S. PATENT DOCUMENTS

| | | | |
|---|---|---|---|
| 3,730,843 | 5/1973 | McKie | 435/23 |
| 3,791,932 | 2/1974 | Schuurs et al. | 435/7 |
| 4,139,415 | 2/1979 | Yin et al. | 435/13 |
| 4,180,437 | 12/1979 | Collen | 435/7 |
| 4,202,872 | 5/1980 | Collen | 436/520 |
| 4,216,291 | 8/1980 | Collen | 435/7 |
| 4,231,999 | 11/1980 | Carlsson et al. | 436/518 |
| 4,298,592 | 11/1981 | Lin et al. | 435/7 |
| 4,298,687 | 11/1981 | Maes | 435/7 |
| 4,458,013 | 7/1984 | Ooyama | 435/23 |

Primary Examiner—Esther M. Kepplinger

[57] ABSTRACT

A new and useful method for assaying proteases, in which an excess of tagged proteinaceous inhibitor of a protease is mixed in solution with a sample containing the protease to form a mixture of a tagged inhibitor-protease complex and free tagged inhibitor. The complex is separated from the tagged inhibitor and the tag measured. Alternatively, anti-protease antibody may be added to bind the complex so that assay specificity and/or separation is enhanced. The method of this invention is applicable to assaying minute quantities of clinically significant proteases e.g. renin, kallikrein, thrombin occurring in serum, plasma, urine and other tissues.

5 Claims, No Drawings

METHOD FOR ASSAYING PROTEASES WITH TAGGED PROTEINACEOUS INHIBITORS

This application is a continuation, of application Ser. No. 317,411, filed Nov. 2, 1981, now abandoned.

INTRODUCTION

This invention relates to new and useful methods for determining or quantifying proteases as unknowns in samples by employing tagged proteinaceous inhibitors of proteases in immunoassays.

BACKGROUND OF THE INVENTION

Previous attempts to quantify or determine an enzyme or its activity involved one of at least four general methods. Enzyme activity can be measured in vivo or in vitro by the ability of an enzyme, generally purified, to hydrolyze its natural substrate to yield a measurable product. Secondly, enzyme activity can also be measured by the ability of an enzyme to hydrolyze a synthetic substrate. Thirdly, an enzyme can be measured by an immunoassay, typically by a radioimmunoassay using tagged anti-enzyme antibody or tagged enzyme. Lastly, an enzyme can also be measured by the use of enzyme inhibitors that are simple organic reagents, not proteinaceous.

All of these methods for quantifying enzymes suffer from the lack of specificity of the tagged binding partner of the enzyme, e.g. natural or synthetic substrate, anti-enzyme antibody or inhibitor, for the enzyme. This lack of specificity is a serious problem with bioassays of enzymes in a biological fluid, wherein the assayed enzyme is often present in extremely small quantities, e.g. urinary kallikrein has a concentration normally in the range of about 150 nanograms of kallikrein/ml in urine normally in the range of 50–300 micrograms of protein/ml. In a biological sample, e.g. urine or plasma, the likelihood that the ligand interacts substantially with undesired proteins is high. For example, diisopropyl-fluorophosphate (DFP) is known to react with a specific serine hydroxyl group in acetyl-cholinesterase [Means, G. E. et al., *Chemical Modification of Proteins* Holden-Day, Inc. (1971), p. 26], yet it will react with a wide variety of enzymes for example serine proteases present in urine.

Bioassays measure biological effects but tend to be tedious, may require expensive animal preparations, are imprecise, and typically rely on hydrolysis of unknown and variable concentrations of native substrates. Radio-immunoassays often provide the greatest sensitivity coupled with good specificity. However, immunoassays generally fail to distinguish active enzyme from inactive enzyme, enzyme precursor(s) or enzyme bound to an inhibitor. Furthermore, radioimmunoassay requires labelled enzyme or labelled antibody, neither of which is inexpensive to prepare and store.

The present invention provides two sources of specificity for an assay of any protease (also known as proteinase) for which naturally-occurring proteinaceous inhibitors are available, whereas previous methods generally provided only one source of specificity. By binding a protease with a tagged inhibitor, i.e. a tagged proteinaceous inhibitor of natural origin, to form protease-inhibitor complexes, then adding anti-protease antibodies, separating protease-inhibitor complexes bound to antibody from the tagged inhibitor, and determining the amount of tag in either the bound or free fraction, the sensitivity of the radioimmunoassay is maintained and the specificity for the active form of a protease is improved. It will be understood that one source of specificity in the protease assay of this invention is the particular binding characteristics of the anti-protease, the other is the particular binding characteristics of the tagged proteinaceous inhibitor.

Furthermore, the present invention is completely different from the "sandwich" assay. The sandwich assay is a method of determining the concentration of an antigen, e.g. a protease, by binding the antigen to its corresponding antibody in solid-phase, then adding tagged purified antibody [Kabat, E. A. *Structural Concepts in Immunology and Immunochemistry* 2nd Ed. Holt, Rinehart and Winston (1976) p. 75; Salmon, S. E. et al. *J. Immunol.* 103, 129 (1969)]. The essential differences are that (1) the sandwich assay requires the use of a tagged purified antibody, preferably $^{125}$I-affinity purified antibody, an expensive and very unstable reagent to make in the laboratory, (2) the sandwich assay does not use a tagged proteinaceous inhibitor of proteases, and (3) the sandwich assay is not an activity assay for an enzyme, particularly a protease.

U.S. Pat. No. 4,134,792 describes a specific binding assay with an enzyme modulator as a labeling substance. The modulator is an inhibitor or allosteric effector and appears to be understood as any simple organic reagent, not a proteinaceous inhibitor. Furthermore, this patent describes an assay substantially different from that of the present invention because the inhibitor is measured by determining the change in the activity of the enzyme, whereas the present invention determines the enzyme by measuring the amount of tagged inhibitor bound to the enzyme.

Several other patents describe methods of isolating naturally occurring proteinaceous inhibitors of proteases or conversely, methods of isolating enzymes that are known to have affinity for such proteinaceous inhibitors of proteases. See, inter alia U.S. Pat. Nos. 3,181,997; 3,558,773; 3,630,841; 3,834,990; 4,030,977. Since these patents describe purification schemes and do not employ a tag on the inhibitor or the enzyme, it is apparent that the novel assay procedure of the present invention is a clearly different and novel use of naturally occurring proteinaceous inhibitors of proteases.

The present invention retains the well-known sensitivity of a radioimmunoassay, but substantially avoids the undesired measurement of denatured enzyme. The present invention avoids the pitfalls typically found in the performance of a radioimmunoassay or a sandwich assay, i.e. preparation of labelled enzyme or of labelled antibody. Enzyme inhibitors, particularly proteinaceous inhibitors, tend to be highly stable and require less expense and time for isolation than the proteases which they bind. Hence it is generally easier to prepare labelled inhibitors than labelled protease. It is well known that labelled, highly purified antibodies are unstable; they tend to break down or denature rapidly even during storage below −60° C.

A wide variety of plasma proteases have naturally occurring proteinaceous inhibitors. Many of the plasma proteins are of substantial importance in the clinical evaluation of disease. They are, for example, involved in blood coagulation, blood clot dissolution, formation and destruction of peptide hormones, complement cascade activation [Laskowski et al. *Ann. Rev. Biochem.* 49, 593 (1980)], and other important natural functions. The present invention encompasses a new and better method of assaying these proteases by measuring their capacity to bind to both a tagged proteinaceous inhibitor and to a specific anti-protease antibody or other appropriately specific binding partner of the protease.

BRIEF DESCRIPTION OF THE INVENTION

The present invention affords a novel and useful method for measuring with great specificity protease in an active conformation by means of a tagged proteinaceous inhibitor which binds to the protease to be assayed. The proteinaceous inhibitor is of natural origin. The selection of proteinaceous inhibitor depends on what protease is to be assayed.

The method of the present invention encompasses a highly specific assay with the following steps: incubation of protase or sample containing protease with tagged proteinaceous inhibitor to form a mixture of tagged inhibitor-protease complexes and free tagged inhibitor, separation of these complexes from the free tagged inhibitor, and measurement of the amount of tag in the complex or measurement of the amount of tag in the free tagged inhibitor. In many instances, antiprotease antibody is added to the mixture to increase the specificity of the assay and/or to enhance the separation of these complexes from free tagged inhibitor.

The method has clear applicability to the measurement of minute quantities of clinically significant, conformationally active proteases found in plasma, urine and other tissues, e.g. thrombin, renin and kallikrein. The method also does not require as much expense and time to prepare the necessary reagents as compared to previous methods e.g. radioimmunoassay and the sandwich assay.

DETAILED DESCRIPTION OF THE INVENTION

This invention encompasses novel methods of assaying undenatured proteases, also called undenatured proteinases, wherein natural peptides that act as inhibitors of proteases are tagged, then bound to the protease to form a complex. To be detectably bound to the protease, the inhibitor of the protease should generally have a binding constant between about $10^5$ and about $10^{15}$ liters/mole. As an additional source of specificity in the assay, it is preferable to use an antibody specific for the protease assayed. This antibody can also provide an easy and convenient method of separating protease bound to the tagged inhibitor of protease from free inhibitor of protease, since the tagged inhibitor of protease is understood to lack substantially detectable interaction with the anti-protease antibody.

The inhibitors of proteases in this invention, hereinafter proteinaceous inhibitors or inhibitors, are naturally occurring small proteins that are known to inhibit the catalytic activity of biologically active proteases. The molecular weight of these small proteins varies from about 1,000 daltons to about 30,000, but may be substantially higher. The low molecular weight contributes to their stability and availability. The most preferable inhibitors are listed in Table 1.

The inhibitors include, but are not limited to proteinaceous inhibitors of the following classes of proteases: serine proteinases, thiol proteinases, carboxyl proteinases, and metallo-proteinases. One of the most important of these classes is the serine proteinases, the proteinaceous inhibitors for which can be divided up into the families listed in Table 2. Aprotinin, also known as Trasylol (Trademark of Bayer) is a member of Family I of Table 2, that is bovine pancreatic trypsin inhibitor (Kunitz) family.

Some natural sources for proteinaceous inhibitors of the thiol, carboxyl and metallo-proteinases are listed in Table 3. For further information on other proteinaceous inhibitors, methods of isolation, amino acid sequences, amino acid compositions, binding specificities, see, inter alia, Laskowski et al., *Ann. Rev. Biochem.* 49, 593 (1980); Perlmann, G. E. et al., eds. *Meth. Enzymol.* 19, 1–1042 (1970); Lorand, L., ed., *Meth. Enzymol.* 45B, 1–939 (1976); Vogel, R. et al., *Natural Proteinase Inhibitors*, Academic Press 1968; Umezawa, H. *Enzyme Inhibitors of Microbiological Origin*, University Park Press, Baltimore 1972.

It will be understood that $\alpha_2$-macroglobulins are not included in the present invention. Because of their size (720,000 daltons) these proteins are known to bury or cover substantially all antigenic determinants upon binding to a protease. Hence anti-protease antibodies, which will not bind an $\alpha_2$-macroglobulin-protease complex, cannot be used to separate the complex from the $\alpha_2$-macroglobulin and free inhibitor. The $\alpha_2$-macroglobulins are also less preferable inhibitors because their binding specificities for proteases are substantially broader than, for example, proteinaceous inhibitors of the serine proteinases. For details, see Laskowski et al., supra.

TABLE 1

| Protease | Inhibitor |
|---|---|
| human glandular kallikrein | aprotinin |
| renin | pepstatin |
| activated Hageman factor | popcorn inhibitor |
| plasma kallikrein | soybean trypsin inhibitor |
| trypsin | soybean trypsin inhibitor |
| trypsin | $\alpha_1$-antitrypsin |
| thrombin | hirudin |
| cathepsin D | pepstatin |
| pepsin | pepstatin |
| thrombin | antithrombin III (in presence of heparin) |
| activated C1 | C1 inactivator |

TABLE 2

Families of protein inhibitors that inhibit serine proteinases

I. Bovine pancreatic tyrpsin inhibitor (Kunitz) family
II. Pancreatic secretory trypsin inhibitor (Kazal) family
III. *Streptomyces subtilisin* inhibitor family
IV. Soybean trypsin inhibitor (Kunitz) family
V. Soybean proteinase inhibitor (Bowman-Birk) family
VI. Potato I inhibitor family
VII. Potato II inhibitor family
VIII. Ascaris trypsin inhibitor family
IX. Other families

TABLE 3

Some inhibitors of thiol, carboxyl, and metalloproteinases

| Enzyme inhibitor | Source of inhibitor | Molecular weight |
|---|---|---|
| Thiol proteinase | | |
| Ficin, papain | Avian egg white | 12,700 |
| Cathepsin B1, C | Avian egg white | |
| bromelain | Pineapple stem | 5,600 |
| Papain, ficin, bromelain | Rat skin | 74,000 |
| | | 13,000 |
| Papain | Rabbit skin | 12,500 |
| Papain, ficin, bromelain | Bauhinia seeds | 24,000 |
| Papain, cathepsin B1 | Leucocyte cell, spleen cell | 15,000 |

TABLE 3-continued

Some inhibitors of thiol, carboxyl, and metalloproteinases

| Enzyme inhibitor | Source of inhibitor | Molecular weight |
|---|---|---|
| Papain, cathepsin B1 | Bovine nasal cartilage | 13,000 |
| Ficin, papain | $\alpha_2$ Serum protein (human) | 90,000 |
| Human liver cathepsin B1 | Immunoglobulin G | |
| Carboxyl proteinase | | |
| Pepsin | *Ascaris lumbriocoides* | 15,500–17,500 |
| Cathepsin D, E | *Ascaris lumbriocoides* | |
| Cathepsin D | Potato | 27,000 |
| Pepsin | *Bauhinia* seeds | 24,000 |
| Pepsin | *Scopolia japonica* cultured cell | 4,000–6,000 |
| Metalloproteins | | |
| Collagenase (human) | Cartilage, aorta (bovine) | 11,000 |
| | Bovine nasal cartilage | 22,000 |
| | Rabbit tissues in culture | 27,500–29,500 |
| | Protein aorta smooth muscle cell in culture | |
| Collagenase (human gastric mucosal) | B1 serum protein | 40,000 |
| $Ca^{2+}$ dependent neutral proteinase | Rat liver | 30,000 |
| Neutral metallo proteinase | Rabbit bone | |
| Carboxypeptidase A, B | Potato | 4,300 |
| Carboxypeptidase A | *Ascaris lumbriocoides* | 7,530 |
| Aminopeptidase | *N. crassa* | 10,000 5,000 |

It will also be understood that the scope of inhibitors of the present invention does not include proteinases that "inhibit" other proteinases by digesting them, e.g. chymotrypsin digestion of trypsin or trypsin digestion of chymotrypsin. The inhibitors of the present invention have only substrates that are enzymes with detectable proteolytic activity. For details, see Laskowski et al., supra.

The present invention requires that a tag be attached to the proteinaceous inhibitor. A radioactive tag is preferred, for example $^{125}I$, $^{131}I$, $^3H$ or $^{14}C$, or any other radioisotope easily and conveniently measured. Tritium labeling of proteins, for example, can be carried out with [$^3H$]-acetic anhydride, a well known reagent frequently used for this purpose. The isotope $^{125}I$ is the most preferred because of its high specific radio-activity and because of its relatively long half life.

A proteinaceous inhibitor can be labelled with $^{125}I$ to a specific activity of about 50 micro Ci/microgram of protein by one of a variety of methods known in the art such as e.g. lactoperoxidase, chloramine-T [Hunter, W. M. et al. *Nature* 194, 495 (1962)], Iodogen [Fraker, P. J. et al. *Biochem. Biophys. Res. Comm.* 80, 849 (1978)], or Bolton-Hunter reagent [Bolton, A. E. et al. *Biochem. J.* 133, 529 (1973)]. The labelled protein is separated from unreacted free $^{125}I$ by gel filtration.

The preferred method of radioactively labelling proteins containing tyrosine is chloramine-T. It is the most frequently used method of labelling proteins with a radioactive tag. Alternatively, one can label tyrosine residues with tritium by the two-step process of first reacting protein with NaI, then catalytically dehydrogenating with tritium gas. If lysine or arginine is not involved in the interaction of proteinaceous inhibitor with protease, then the free amino group of the side chains of these amino acids can be labelled with $^3H$-acetic anhydride or with Bolton Hunter reagent.

Aprotinin is known to contain 4 tyrosine residues [Huber, R. et al. *Naturwissen* 57, 389 (1970)], and labelling with chloramine-T does not substantially reduce its binding to kallikrein. Bolton Hunter or [$^3H$]-acetic anhydride labelling does not work, possibly because of acylation of the $Lys^{15}$ residue known to be required for the formation of the inhibitor-protease complex [Huber, R. supra (1970)]. Labelling aprotinin with chloramine T is preferred to the two-step reacton with NaI and $^3H$ gas because $^{125}I$ or $^{131}I$ have much higher specific radioactivities than tritium.

Pepstatin, an inhibitor listed in Table 1, is known to have a free amino group but no tyrosine residue [Aoyagi, T. et al. in Reich, E. et al (eds.) *Proteases and Biological Control*, Cold Spring Harbor 1975 pp. 429–454]. Since substitution of the free amino group with a variety of alkanoyl groups does not affect inhibiting activity, then the Bolton-Hunter and [$^3H$]-acetic anhydride are each most likely to work as labelling reagents.

A large variety of other tags can be employed instead of radioactive ones. Other methods of tagging the inhibitor include attachment of a fluorogen, chromophore, enzyme or luminescent tag. For example horse radish peroxidase or beta-galactosidase may be coupled to the proteinaceous inhibitor by many of the methods discussed in Kennedy, J. H. et al., *Clinica Chimica Acta* 70, 1 (1976). Fluorescein isothiocyanate is a well known fluorogenic group that can be attached to proteins [Ackroyd, J. F. ed., *Immunological Methods*, Blackwells Oxford (1964) pp. 155–174].

The incubation of protease with tagged inhibitor can lead to the formation of detectable tagged inhibitor-protease complexes under a variety of conditions. Preferably, a quantity of tagged inhibitor is used that is in excess of the quantity of protease, since there is thought to be a simple and rapid equilibrium between protease and free inhibitor on the one hand and the complex on the other [Laskowski et al, supra]. Because the equilibrium constant for the association of protease and its proteinaceous inhibitor is extremely high (in the range of $10^7$–$10^{13}$ liters/mole), incubation to equilibrium is a rapid method of assaying the protease of this invention. Equilibrium can be experimentally determined, for example, as the time of incubation after which complex formation does not detectably increase or decrease.

This invention also encompasses incubation conditions that are far from equilibrium, wherein it is possible to incubate a quantity of protease in excess of the quantity of tagged inhibitor and still be able to quantify the amount of protease. What should be avoided are conditions wherein substantially all of the tagged inhibitor would be bound to the proteases, i.e. there would be undetectable changes in binding of inhibitor to its protease with small changes (e.g. increasing or decreasing by a factor of 0.5) in the concentration of protease For a general discussion on kinetics as it can be applied to the interaction of proteases and their inhibitors see Lehninger, A. L. *Biochemistry* Worth New York pp. 186–195, and Laskowski et al, supra.

In addition to a proteinaceous inhibitor of proteases, and a tag attached to it, measurement of proteases with this reagent also requires a method of separating tagged inhibitor bound to enzyme, also called inhibitor-protease complexes, from the tagged inhibitor. Typically there is an excess of tagged inhibitor with respect to the concentration of enzyme.

The preferable method of separating inhibitor-protease complexes from free inhibitor is to react the mixture of inhibitor and protease with an antiserum specific for the protease. The antiserum provides a second source of specificity for the assay, but it is contemplated that some inhibitors of this invention are specific enough for the protease to render use of anti-protease antibody unnecessary.

Substantial quantities (about 1 liter) of antiserum with high titer of anti-protease antibodies can be made with about 100 micrograms of purified protease, an amount often not prohibitively expensive or time consuming to obtain. It will be understood that a variety of immunization protocols can be employed to obtain such antisera, in this case antisera specific for any one of the proteases of this invention. These protocols are well known to practicing immunologists, and can be illustrated, by way of examples, as an emulsion of about a one-to-one ratio (v/v) of protease (1 mg/ml) with complete Freund's adjuvant, or an emulsion of about a one-to-one ratio of protease (1 mg/ml) with incomplete Freund's adjuvant. In the preferred mode of the invention, protease is injected into rabbits on a low dose injection schedule (about 10 micrograms per injection).

If an antibody is used in the assay of this invention, and it preferably is, there are a large variety of methods to separate protease bound to antibody from unbound protease. One of the simplest approaches is to precipitate the antibody with an anti-antibody, also called a double antibody. Generally, precipitation with double antibody can be performed by adding enough non-specific antiserum to the anti-protease antibody to raise the concentration of precipitable antibody to near the equivalence zone, then adding the anti-antibody. Alternatively, and preferably, one can use anti-antibody covalently bound to an insoluble support, such as e.g. bromoacetyl cellulose, acrylamide beads with azide groups attached, or agarose beads esterified with N-hydroxysuccinimide. Packing and settling by these solid-phase immunoadsorbents can be assisted by the addition of milk of magnesia. Among other known techniques for separating protease bound to antibody from unbound protease are those using solid support matrices, wherein glass, silica or unitary plastic inserts are used to fix one component of the antigen-antibody pair. An antibody attached to an insoluble support is thought to bind its antigen virtually irreversibly, unlike a double antibody, which is in solution. Another well known technique is to insolubilize the double antibody itself, usually by cross-linking with glutaraldehyde.

Another approach is to bring down antibody or anti-antibody with protein A preferably either in the form of the whole cell *S. aureus* or in the form of the purified protein conjugated to an insoluble support, e.g. protein A-Sepharose CL-4B.

Instead of using another protein with a binding affinity for the anti-enzyme antibody, one can precipitate the antienzyme antibody with salts such as ammonium sulfate or zirconyl phosphate (z-gel), or with polyethylene glycol. Among other known techniques are those using solid support matrices, also known as a solid-phase assay wherein glass, silica or plastic beads or unitary plastic inserts are used to fix one component of the antigen-antibody pair.

An alternative embodiment of this invention is to separate protease-tagged inhibitor complexes from free tagged inhibitor without an anti-protease antibody. The specificity of the inhibitor should be demonstrated to be solely for the protease assayed before one can dispense with the use of the anti-protease. Unfortunately, many of the inhibitors of this invention bind to more than one protease, e.g. $\alpha_1$-proteinase inhibitor binds to $\alpha_1$-protease and to trypsin. Hence the safest and most specific way to assay proteases in body fluids or in other tissue samples is to employ an anti-protease antibody as an additional source of specificity in the assay of this invention.

Methods of separating inhibitor-protease complexes from free protease and free inhibitor include the well-known biochemical techniques of anion exchange chromatography with e.g. DEAE-cellulose and a salt gradient, cation exchange chromatography with e.g. carboxymethyl cellulose and a salt gradient, gel filtration with e.g. Sephadex G-25 or Bio-Gel P-200, and equilibrium dialysis. Equilibrium dialysis will work with only small peptide inhibitors of the invention, e.g. pepstatin, because larger inhibitors cannot penetrate the pores of a dialysis membrane.

EXAMPLE 1

Assay of human urinary kallikrein with $^{125}$I-labelled aprotinin

Aprotinin was reacted with Na$^{125}$I by the method of Hunter, W. M. and Greenwood, F. C. *Nature* 194, 495–496 (1962) to yield $^{125}$I-aprotinin at a specific radioactivity of 80 $\mu$Ci/$\mu$g. The labelled aprotinin and pure human urinary kallikrein were dissolved separately in the assay buffer, 0.05M Tris HCl, pH 7.4, plus 0.1% gelatin. Antibody specific for human urinary kallikrein was covalently bound to Affi-gel (BioRad Laboratories) and the gel was suspended in the assay buffer. Fresh human urine samples were treated by application of 500 $\mu$l of a given sample to a 0.5 $\times$ 10 cm column of Sephadex G-25 (Pharmacia Fine Chemicals) equilibrated and developed with the assay buffer. Samples of the first 1.5 ml of buffer to pass through the column after the sample application were assayed for their contents of kallikrein, an enzyme not retained by Sephadex G-25. Each assay tube contained buffer, buffered $^{125}$I-aprotinin (100,000 cpm), a measured quantity of pure kallikrein or chromatographed urine sample, and antibody-Affi-gel beads, all in a total volume of 200 $\mu$l. The reaction mixtures were incubated at 37° C. for 2 hours and then 50 $\mu$l of milk of magnesia (Sterling Drugs) was added to each tube. Milk of magnesia assists in the packing of insoluble polymeric beads such as Affi-gel. The tubes were assayed for $^{125}$I by gamma-counting and then were centrifuged. The supernatant of each was removed by decantation, and the precipitate was assayed for $^{125}$I (aprotinin bound to kallikrein bound to antibody covalently bound to Affi-gel, in milk of magnesia). Results, expressed as % binding of $^{125}$I (cpm of the precipitate+c.p.m. of the total reaction mixture$\times$100), are shown in the Table.

TABLE

| Binding of $^{125}$I-aprotinin to human urinary kallikrein | |
|---|---|
| kallikrein (in nanograms) | % binding of $^{125}$I |
| 0 | 3.01% |
| 0.1 | 3.09 |
| 0.25 | 3.20 |
| 0.5 | 3.40 |
| 1.0 | 4.20 |
| 2.5 | 5.64 |
| 5.0 | 8.52 |
| 10.0 | 13.46% |

From a standard curve constructed from the data of the Table, the urine samples from human volunteers, were found to contain kallikrein as shown below:

| Subject | Kallikrein (nanograms/ml of urine) |
| --- | --- |
| W. G. | 200 |
| D. M. | 376 |
| D. B. | 50 |
| G. M. | 36 |

EXAMPLE 2

Assay of plasma renin with $^{131}$I-labelled pepstatin

A series of 12×75 mm polyethylene tubes are precoated with antiserum to plasma renin by adding 250 µl of a 1:1000 dilution of the antiserum to each of the tubes. Incubation conditions, buffers and washing are according to Catt et al. *Science* 158, 1570 (1967). $^{131}$I-pepstatin (about 100,000 cpm, 90 µCi/µg) in 10 µl of assay buffer (0.05M Tris HCl buffer pH 7.4, 0.15M NaCl, 0.1% gelatin) is then added. Unlabelled pepstatin is available from Sigma Chemical Co. Then 190 µl of either buffer, pure renin in buffer or anticoagulant-treated plasma (diluted 1:100 in buffer) is added to yield a total volume of 200 µl. The reaction mixtures are incubated at 37° C. for 2 hours and then the tubes are washed three times with 1 ml of assay buffer. The tubes are counted in a gamma counter.

EXAMPLE 3

Assay of plasma thrombin with $^3$H-hirudin and anti-thrombin antibodies coupled to cellulose Hirudin (Sigma Chemical) is tritiated with [$^3$H]-acetic anhydride to yield a specific activity of $10^4$–$10^5$ cpm/µg. An antiserum containing anti-thrombin antibodies is coupled to bromoacetyl cellulose (Miles Laboratories) as per Jagendorf, A. T. et al *Biochim. Biophys. Acta* 78, 516 (1963). Thrombin is inexpensive and can be purchased from Sigma Chemical Co.

To a 1.5 ml polypropylene microcentrifuge tube (Brinkmann) is added 10 µl containing 3,000 cpm of $^3$H-hirudin in assay buffer (0.05M Tris-HCl, pH 7.4, 0.15M NaCl, 0.1% gelatin), and either 10 µl of purified thrombin (1–1,000 ng) in assay buffer, or 10 µl of assay buffer as a control. The tubes are capped and placed in a 37° C. water bath for 2 hours. Then 200 µl of cellulose-coupled to anti-thrombin antibodies (about 100 µg/ml in assay buffer) is added to each tube, the mixtures are briefly mixed by hand, and let stand at room temperature 45 minutes. The tubes are centrifuged 5 minutes at 10,000 xg in an Eppendorf microcentrifuge and 125 µl of the supernatant is counted.

EXAMPLE 4

$^{125}$I-labelling of aprotinin and purification of active conformer

Aprotinin (Trasylol, trademark of Bayer) was labelled by the technique of Hunter et al. *Nature* 194, 495 (1962). 1 mCi of Na$^{125}$I in 20 µl of 0.5M sodium phosphate buffer, pH 7.4, was mixed with 10 µl (25 µg) of chloramine T (Eastman Kodak) in the same buffer. Aprotinin, 2 µg in 10 µl of the buffer, was added, and the reaction was allowed to proceed for 75 sec at 22° C. Na$_2$S$_2$O$_5$, 100 µg in 40 µg of the buffer, was added to stop the reaction. Labelled aprotinin was separated from $^{125}$I by chromatography (1.15×45 cm column) on Bio-Gel P-2 (BioRad Laboratories) equilibrated and developed with 0.05M Tris HCl buffer, pH 7.4 plus 0.15M NaCl and 0.1% gelatin. Column fractions (1.8 ml/fraction) were analyzed for radioactivity and for their ability to inhibit the hydrolysis of (D)Pro-Phe-Arg[$^3$H]benzylamide by apparently pure human urinary kallikrein. (D)Pro-Phe-Arg-[$^3$H]benzylamide (from Ventrex Laboratories, Inc.) was used in a final concentration of 40 nM in 0.05M Tris HCl, pH 9.5, essentially as described by Chung et al. *Adv. Exp. Med. Biol.* 120A, 115 (1979) for Pro-Phe-Arg-[$^3$H]benzylamide. Kallikrein was used in a final concentration of 200 pM. The results showed that there was a peak of inhibiting activity that coincided with the peak of $^{125}$I-protein eluting in the void volume.

EXAMPLE 5

Preparation of anti-human urinary kallikrein bound to a solid support

Antibodies to human urinary kallikrein were prepared as described by Oza and Ryan, *Biochem. J.* 171, 285 (1978). The crude antiserum was acidified with 1N HCl to pH 2.2. After 30 minutes at room temperature, the antiserum was neutralized to pH 7.5 and then heated at 56° C. for 2 hours to inactivate complement. The IgG fraction was obtained by chromatography on DE-52 cellulose (Whatman) as described by Ryan et al., *Tissue and Cell* 8, 111 (1976). Affi-gel 10 (a N-hydroxysuccinimide ester of agarose; BioRad Laboratories), 5 ml settled vol., was washed 3 times with 15 ml of isopropanol and 3 times with cold H$_2$O. The gel was suspended in 5 ml of 0.1M NaHCO$_3$, pH 8.0, and was reacted with 5 ml (4.4 mg of protein/ml) of the IgG fraction of anti-kallikrein, all at 4° C. The reaction mixture was gently agitated for 4 hrs. at 4° C. and then was mixed with 200 µl of 1.0M glycine ethyl ester. The reaction mixture was continued for 1 hr. at 22° C. The gel was washed 3 times with 15 ml portions of 0.1M NaHCO$_3$. Coupling of IgG was reasonably efficient (approx. 79%). The gel was stored in 0.1M NaHCO$_3$, containing 0.02% NaN$_3$ until used.

While the invention has been described in connection with specific embodiments thereof, it will be understood that it is capable of further modifications and this application is intended to cover any variations, uses, or adaptations of the invention following, in general, the principles of the invention and including such departures from the present disclosure as are obvious to one of ordinary skill in the art to which the invention pertains and as may be applied to the essential features hereinbefore set forth, and as follows in the scope of the appended claims.

What is claimed is:

1. A method of determining or quantifying proteases with a proteinaceuous inhibitor of natural origin which comprises the steps of:
   a. providing in solution a quantity of protease and a quantity of tagged proteinaceons inhibitor of said protease, said quantities being so selected that they form in step (b) detectable tagged inhibitor-protease complexes;
   b. incubating said protease and said inhibitor to form a mixture comprising said complexes and free tagged inhibitor;
   c. further incubating said mixture of detactable tagged inhibitor-protease complexes and free tagged inhibitor with antibody specific for said protease to form a second mixture of detectable tagged inhibitor-protease antibody complexes and free tagged inhibitor, then d. separating said inhibitor-protease antibody complexes from said free tagged inhibitor, and e. measuring the amount of tag in said complexes or measuring the amount of tag in said free tagged inhibitor, and wherein said complex as recited in step (e) is an inhibiting-protease antibody complex.

2. A method according to claim 1 wherein the quantity of tagged proteinaceous inhibitor is greater than the quantity of protease.

3. A method according to either of claims 1 and 2 wherein said antibody specific for said protease is in solid phase.

4. A method according to claim 3 wherein said antibody is covalently attached to polyacrylamide beads.

5. A method according to claim 4 wherein step (e) is performed in the presence of milk of magnesia.

* * * * *